| United States Patent [19] | [11] Patent Number: 4,780,475 |
| Cerra et al. | [45] Date of Patent: Oct. 25, 1988 |

[54] PREPARATION FOR THE PREVENTION OF CATABOLISM

[76] Inventors: Frank B. Cerra, 4522 Arden Ave., S.E. Edina, Minn. 55424; Ronald J. Amen, 18101 Catherine Cir., Villa Park, Calif. 92667

[21] Appl. No.: 945,429

[22] Filed: Dec. 22, 1986

Related U.S. Application Data

[63] Continuation of Ser. No. 825,307, Feb. 3, 1986, abandoned, which is a continuation of Ser. No. 715,502, Mar. 25, 1985, abandoned, which is a continuation of Ser. No. 537,595, Sep. 30, 1983, abandoned.

[51] Int. Cl.[4] .................... A61K 31/40; A61K 31/195
[52] U.S. Cl. ..................................... 514/408; 514/561
[58] Field of Search ................................ 514/408, 561

*Primary Examiner*—Stanley J. Friedman
*Attorney, Agent, or Firm*—Gerald D. Sharkin; Robert S. Honor; Walter F. Jewell

[57] ABSTRACT

Prevention of catabolism and increasing protein synthesis in a subject undergoing stress with compositions containing isoleucine, leucine and valine.

15 Claims, No Drawings

PREPARATION FOR THE PREVENTION OF CATABOLISM

This is a continuation of application Ser. No. 825,307, filed Feb. 3, 1986, which in turn is a continuation of application Ser. No. 715,502, filed Mar. 25, 1985, which in turn is a continuation of application Ser. No. 537,595, filed Sept. 30, 1983, all of which are now abandoned.

This invention relates to an amino acid preparation for enteral administration to prevent catabolism and to increase protein synthesis in subjects undergoing severe metabolic stress.

Under normal nutritional and physiological conditions, fuel requirements of the body are largely met by glucose and fatty acids metabolism. The body's amino acids generally contribute little towards overall fuel economy at these times. However, during abnormal metabolic stress states induced by trauma or sepsis, fat mobilization and utilization and glucose utilization are decreased due to hormonal changes precipitated by the stress. Under these conditions, an extremely high and rapid rate of muscle protein catabolism occurs. A consequence of this catabolism is the liberation of branched chained amino acids (BCAA), namely, isoleucine, leucine and valine from the bound protein state to the free amino acid state. In the free state, the BCAA are readily available to be further catabolized to yield energy to help satisfy the energy deficit caused by metabolic stress.

Over the last several years, investigators have studied the relationship between BCAA and the metabolic consequences of trauma in man. Most of these studies concerned themselves with understanding cause and effect, as it related to biochemistry and metabolism, and subsequent physiological responses. A few studies were designed to observe the change induced in a traumatized man or in an animal model when nutritional or pharmacological doses of BCAA, either alone or in combination with other amino acids, were given to the stressed subject. In these studies, the amino acids were administered to the patient or animal as a parenteral solution. There are no publications, to date, that describe studies in stressed or traumatized patients using oral doses of either the BCAA alone or in combination with other amino acids. No adverse effects attributable to the parenteral amino acid solutions have been found. However, there are problems with intravenous nutritional support and the central venous catheter needed and with the well-known metabolic effects (liver function test changes; fluid and electrolytes) that are usually of little or no clinical consequence in well-managed patients. Because of the problems related to the parenteral route of administration, it would be advantageous if an enteral formulation could be administered to stressed patients that is more suited to their nutritional needs. It has now been discovered that gastrointestinal motility is more than adequate in stressed or traumatized subjects and that absorption does occur effectively to an unexpected extent in these patients.

The present invention provides an enteral preparation for use in stressed patients, which significantly improves nitrogen retention by decreasing muscle protein catabolism and markedly improving protein synthesis. The preparation provides 1.25 to 3.25 grams of protein per kilogram of body weight per day (gm/kg/day), preferably 1.5 to 2.5 gm/kg/day and more preferably 1.5 to 2.0 gm/kg/day. In the preparation, 40 to 50%, preferably 40 to 45%, by weight of the total amino acids are the branched chain amino acids, isoleucine (Ile), leucine (Leu) and valine (Val). The ratio of Ile:Leu:Val is 0.5 to 1.5 : 1.5 to 2.5 : 0.5 to 1.5. Preferably, the amount of Leu is greater than the amounts of either Ile or Val (Ile <Leu >Val); and more preferably, the ratio of Ile:Leu:Val is 1:2:1.

In addition to the isoleucine, leucine and valine, the preparation also contains essential and non-essential amino acid. The amounts of the amino acids can vary, but the preferred preparation contains the following parts by weight of amino acids per 100 parts of total amino acids:

| Essential Amino Acids | |
| --- | --- |
| L-Isoleucine | 11.0 |
| L-Leucine | 22.0 |
| L-Valine | 11.0 |
| L-Tryptophan | 1.5 |
| L-Phenylalanine | 4.0 |
| L-Methionine | 3.0 |
| L-Lysine | 6.5 |
| L-Threonine | 5.0 |
| Non-Essential Amino Acids | |
| L-Arginine | 7.0 |
| L-Tyrosine | 0.7 |
| L-Cysteine | 1.0 |
| L-Alanine | 5.5 |
| L-Glutamic Acid | 7.8 |
| L-Aspartic Acid | 3.5 |
| L-Histidine | 3.5 |
| L-Serine | 2.0 |
| Glycine | 3.0 |
| L-Proline | 2.0 |

The above amino acids can be used as such or in the form of a pharmaceutically acceptable salt. The amino acid preparation is preferably administered with additional carbohydrate or fat energy sources and with vitamins and minerals, as required. Modified carbohydrates and fats specifically designed for stressed subjects are especially preferred. The carbohydrates, fats, vitamins and minerals can be administered in the same solution as the amino acids or separately. It is preferred however, that these five component groups be separately packaged to facilitate tailoring of the diet to the patients specific needs. In addition to the above, the formulations may include preservatives or stabilizers, as required, such as ascorbic acid, or other compatible preservative agents. Nitrogen gas may also be used to protect the preparation in solution form.

The following examples further illustrate the present invention but are not meant to be limiting.

EXAMPLE 1

In this example, the preparation of the instant invention is compared with a comercially available product containing 15.6 % BCAA. The diets used have the following approximate amino acid compositions in grams per 100 grams of amino acid present.

| Amino Acid | Commercial Product | Invention Product |
| --- | --- | --- |
| Essential Amino Acids | | |
| Isoleucine | 4.2 | 11.0 |
| Leucine | 6.5 | 22.0 |
| Lysine | 4.9 | 6.5 |
| Methionine | 4.6 | 3.0 |
| Phenylalanine | 7.1 | 4.0 |
| Threonine | 4.2 | 5.0 |

-continued

| Amino Acid | Commercial Product | Invention Product |
| --- | --- | --- |
| Tryptophan | 1.3 | 1.5 |
| Valine | 4.6 | 11.0 |
| Non-Essential Amino Acids | | |
| Alanine | 5.2 | 5.5 |
| Arginine | 4.1 | 7.0 |
| Aspartic acid | 11.1 | 3.5 |
| Cysteine | — | 1.0 |
| Glutamic acid | — | 7.8 |
| Glutamine | 18.2 | — |
| Glycine | 9.8 | 3.0 |
| Histidine | 2.4 | 3.5 |
| Proline | 6.9 | 2.0 |
| Serine | 4.2 | 2.0 |
| Tyrosine | 0.9 | 0.7 |

The diets are administered in the form of a 300 milliliter aqueous dilution containing 12.5 grams of the amino acid, 0.26 grams of corn oil, 63.31 grams carbohydrates, 3.9 grams of salt and vitamins. In this form, both diets provide 300 calories per kilogram (kcal/kg) of animal body weight per day.

In this test, male Sprague-Dawley rats weighing 175 to 225 gm are used in the experiments. Prior to the study, all the animals are housed and fed standard laboratory chow and tap water for a minimum of 4 days. Under sodium pentobarbital anesthesia (25 mg/kg body weight), a Silastic catheter (0.20 inch ×0.37 inch) is inserted through the external jugular vein into the superior vena cava. The tube is tunneled subcutaneously and brought out through a stab wound in the skin of the mid-scapula region. Another silastic tube (0.25 inch ×0.47 inch) is placed in the fundus of the stomach, tied tightly around a needle bridge and tunneled subcutaneously to the infrascapular area. Both external tubings are passed through a teflon 'button' and stainless steel spring, and the intragastric tube is attached to a flow-through swivel. The intravenous tube is locked with a heparin seal until the day of the infusion. After catheterization, the femurs of each leg are surgically exposed by blunt dissection and fractured with forceps. The fractured femurs are then packed with approximately 1 cm$^3$ of cotton gauze which previously is cultured for 18 to 24 hours at 37° C. in 10 ml of thioglycollate media with 2 gm of fresh cecal contents. The wounds are closed and the animals are placed in metabolic units. For the next three days the animals receive 59±5 ml of one of the two enteral diets. For the last 3 hours, while the nutrients are being administered, the rats are housed in metabolic chambers that permit collection and analysis of the expired breath. A tracer quantity of L-(1-$^{14}$C) leucine is simultaneously infused through the central venous catheters that the radioactivity was delivered at a rate of 1.0 uCi/H. Total carbon dioxide production and the appearance of $^{14}$C radioactivity in the expired breath are determined at 30 minute intervals. At the end of the infusion, the rats are decapitated and mixed arterial-venous blood is collected from the neck into heparinized tubes. Samples of liver and rectus abdominus muscle are rapidly removed, homogenized in weighed vials containing 5 ml. of 10% sulfosalicylic acid in ice cold containers and stored at −30° C. Another sample of 1 gram of liver is stored in 4 ml. of saline at −30° C. for determination of total liver nitrogen. Plasma samples are separated and stored at −30° C.

Total carbon dioxide production and the appearance of $^{14}$CO$_2$ are determined at ½ hour intervals as described by Kawamura, I., Moldawer, L. L., Keenan, R. A., et al: Altered amino acid kinetics in rats with progressive tumor growth; Cancer Research 42:824–829 (1982). Free leucine specific radioactivity is determined using the methodology of Moldawer et al. (Moldawer, L. L., O'Keefe, S. J. D., Bothe, A., Jr., et al: In vivo demonstration of the nitrogen sparing mechanisms of glucose and amino acids in the injured rat; Metabolism 29:173–180, 1980). After determination of total concentration of plasma, amino acids and radioactivity with a Beckman LS-8000 Spectrometer, aqueous samples of infusate, plasma, intracellular fluid, and protein are also analyzed for total radioactivity using the Moldawer et al methodology. Total urinary nitrogen and liver protein are determined following a micro-Kjeldahl digestion. (Moldawer, L.L., Bistrian, B. R., Blackburn, G. L.: Factors determining the preservation of protein status during dietary protein deprivation; J. Nutrition 111:1287–1296, 1981). Plasma transferrin levels are determined by radioimmunoassay. Plasma ketoisocaproate is eluted off a C$_{18}$-reverse phase 10u Bondapak column using a 95% phosphate buffer (pH 7.0), 5% acetonitrile solution at 0.9 mls/min. The plasma ketoisocaproate is detected at 210 nm and the peaks are manually collected for liquid scintillation spectrometery. (Echenique, M. M., Moldawer, L. L., Bistrian, B. R., et al: Improvement in amino acid utilization in the critically ill with parenteral formulas enriched with branched chain amino acids: Gastroenterology, 1983). Rates of whole body leucine appearance, oxidation and incorporation into whole body protein are determined using the stochastic model of Waterlow et al. (Waterlow, J. C., Garlick, P. J., Millward, D. J.: Protein Turnover in Mammalian Tissues and in the Whole Body, New York, Elsevier-North Holland Publishers, 1978). Because these measures rely on the plasma leucine specific radioactivity to accurately reflect the specific radioactivity of leucine at its true site of oxidation, the specific radioactivity of leucine's ketoacid, ketoisocaproate, is also measured and is assumed to be better representative of the true precursor pool (Schwartz, H. P., Matthews, D. E., Yang, R. D., et al: Relationship of plasma leucine and ketoisocaproate during a L-(1-$^{13}$C) leucine infusion in man. A method for measuring human intracellular leucine enrichment; Metabolism 31:1105–1113, 1982). Fractional rates of protein synthesis in individual tissues are determined from the product-precursor ratio obtained at the end of the isotope infusion, using the equation of Garlick et al. (Garlick, P. J., Millward, D. J., James, W. P. T.: The diurnal response of muscle and liver protein synthesis in vivo in meal-fed rats; Biochem. J. 136:935–945, 1973).

After three days of enteral feeding, both groups of injured animals show similar changes in nitrogen balance and no difference is found in plasma transferrin levels. Plasma amino acid profiles show significant changes; most of which are attributable to the nature of the diet. The rats that receive the branched chain amino acid enriched formula of this application have significantly higher plasma levels of leucine, valine, and isoleucine and significantly lower concentrations of serine, glutamine, phenylalanine and tyrosine. Both diets contain similar amounts of alanine and the group that received the branched chain amino acid enriched formula has lower levels of alanine in the plasma concentrations than the commercial product group. This would suggest that the alanine shuttle for gluconeogenesis is reduced, due probably to a reduced breakdown of muscle protein or an increase in protein synthesis, indicating a better utilization of amino acids by skeletal muscle.

Analysis of whole body leucine kinetics demonstrate that the group that receive the branched chain amino acid enriched formula have a higher percentage of leucine appearance oxidized and a greater incorporation of plasma leucine into newly synthesized protein than in the group that receive the commercial product. The fractional synthetic rate in the hepatic tissue is significantly higher for the group that receive the branched chain amino acid enriched formula. In skeletal muscle, synthesis rates also appear greater. Oxidation rates of total body leucine as measured using ketoisocaproate are significantly higher in the branched chain amino acid enriched group; but the net balance of leucine, like nitrogen balance, is unchanged. In conclusion, an enteral diet containing 44% BCAA by weight of the total amino acids present restores normal amino acid concentrations and better support protein synthesis than similar diets containing less quantities of these acids.

EXAMPLE 2

A packet containing 15.4 grams of the following amino acid components in the amounts indicated is prepared by standard procedures.

| Amino Acid | Amount (gm) |
| --- | --- |
| L-Isoleucine | 1.6 |
| L-Leucine | 3.3 |
| L-Valine | 1.6 |
| L-Tryptophan | 0.2 |
| L-Phenylalanine | 0.6 |
| L-Methionine | 0.4 |
| L-Lysine (as L-Lysine Acetate) | 1.0 |
| L-Threonine | 0.8 |
| L-Arginine | 1.0 |
| L-Tyrosine | 0.1 |
| L-Cysteine | 0.2 |
| L-Alanine | 0.8 |
| L-Glutamic Acid | 1.2 |
| L-Aspartic Acid | 0.5 |
| L-Histidine | 0.5 |
| L-Serine | 0.3 |
| Glycine | 0.4 |
| L-Proline | 0.3 |

Each packet provides 15.0 grams of essential and non-essential amino acids and 2.1 grams of nitrogen and has a caloric content of 60 calories. The amino acids are optionally administered enterally with vitamins and minerals in the amounts required, carbohydrates such as monosaccharide, sugar, corn syrup sugar, maltodextrins and the like and/or fats, such as safflower oil, corn oil, medium chain triglycerides and the like, as an aqueous formulation.

EXAMPLE 3

A clinical study was carried out with the product of example 2 using ten patients ranging in age from 20 to 80 years. The group consisted of seven male patients with an average age of 57 years and three female patients with an average age of 53 years. All of the patients were quantitatively malnourished at entrance to the study and were undergoing active sepsis requiring intensive care. Approximately 30 calories and 0.22 grams of nitrogen per kilogram were administered to each patient per day. For the majority of the patients, an average of 21.4% of the calories came from the amino acid preparation of example 2 and 78.6% came from non-protein components. The nonprotein components were corn syrup solids (four calories per gram), which provided an average of 71.3% of the daily calories, and a mixture essentially of safflower oil and medium chain triglycerides (nine calories per gram), which provided an average of 7.3% of the daily calories. Vitamin and minerals, as required, were also given to the patients. The diet was administered to three of the patients through a tube surgically placed in the jejunum. The remaining seven patients received the diet nasogastrically—four into the stomach and three into either the duodenum or jejunum of the small intestine. The average caloric density of the aqueous formulation administered was 1.1 calories per milliliter.

The following average nitrogen balances were found:

| Day | Gm. $N_2$/day | Day | Gms. $N_2$/day |
| --- | --- | --- | --- |
| 1 | $-3.6 \pm 6.1$ | 5 | $1.4 \pm 8.3$ |
| 2 | $0.2 \pm 7.3$ | 6 | $0.5 \pm 6.4$ |
| 3 | $0 \pm 7$ | 7 | $1.2 \pm 7.5$ |
| 4 | $0.9 \pm 7.7$ | | |

Gut absorption was excellent with approximately 90% of the nitrogen absorbed in those patients with a complete gastrointestinal tract. In those patients with fistular or shortened bowels, absorption fell but was generally in the 60 to 75% range. The one pateint with an ileostomy started in the 80% absorption range, but increased to the 90% level rapidly. The fact that the formulation could be administered enterally to patients this ill as well as the levels of nitrogen absorption found were completely unexpected. In addition, transferrin levels were unexpectedly elevated indicating that the formulation supported liver function and protein synthesis in a manner never previously reported. In the testing, the formulation was also found to be safe and without detectable side-effects.

What is claimed is:

1. A method of preventing catabolism and increasing protein synthesis in a subject undergoing metabolic stress, which comprises administering enterally to the subject 1.25 to 3.25 grams of essential and non-essential amino acids per kilogram of subject body weight per day, wherein the amino acids comprise by weight of total amino acids 40 to 50% isoleucine, leucine and valine in a ratio by weight of 0.5 to 1.5 parts of isoleucine to 1.5 to 2.5 parts of leucine to 0.5 to 1.5 parts of valine.

2. A method according to claim 1, wherein the amino acids comprise by weight of total amino acids 40 to 45% isoleucine, leucine and valine.

3. A method according to claim 1, in which 1.5 to 2.5 grams of amino acids per kilogram of subject body weight are administered per day.

4. A method according to claim 1, in which 1.5 to 2.0 grams of amino acids per kilogram of subject body weight are administered per day.

5. A method according to claim 3, in which the ratio of isoleucine to leucine to valine is 1 to 2 to 1.

6. A method according to claim 1, in which the amino acids comprise per 100 parts of total amino acids 11.0 parts of L-isoleucine; 22.0 parts of L-leucine; 11.0 parts of valine; 1.5 parts of L-tryptophan; 4.0 parts of L-phenylalanine; 3.0 parts of L-methionine; 6.5 parts of L-lysine; 5.0 parts of L-threonine; 7.0 parts of L-arginine; 0.7 part of L-tyrosine; 1.0 part of L-cysteine; 5.5 parts of L-alanine; 7.8 parts of L-glutamic acid; 3.5 parts of L-aspartic acid; 3.5 parts of L-histidine; 2.0 parts of L-serine; 3.0 parts of glycine and 2.0 parts of L-proline.

7. A pharmaceutical composition for enteral administration in preventing catabolism and increasing protein synthesis in a subject undergoing metabolic stress which comprises essential and non-essential amino acids in an amount sufficient to provide 1.25 to 3.25 grams of amino acids per kilogram of subject body weight per day, wherein the amino acids comprise by weight of total amino acids 40 to 50% isoleucine, leucine and valine in a ratio by weight of 0.5 to 1.5 parts of isoleucine to 1.5 to 2.5 parts of leucine to 0.5 to 1.5 parts of valine.

8. A pharmaceutical composition according to claim 7, wherein the amino acids comprise by weight of total amino acids 40% to 45% isoleucine, leucine and valine.

9. A composition according to claim 7, in which 1.5 to 2.5 grams of amino acids per kilogram of subject body weight are administered per day.

10. A composition according to claim 7, in which 1.5 to 2.0 grams of amino acids per kilogram of subject body weight are administered per day.

11. A composition according to claim 7, in which the ratio of isoleucine to leucine to valine is 1 to 2 to 1.

12. An enteral preparation comprising a composition according to claim 7 and carbohydrate and fat in an amount effective for the treatment of the stressed subject and an aqueous carrier therefor.

13. A composition according to claim 12, in which vitamins and minerals in amounts effective for the treatment of the stressed subject are administered.

14. A composition according to claim 7, in which the amino acids comprise per 100 parts of total amino acids, 11.0 parts of L-isoleucine; 22.0 parts of L-leucine; 11.0 parts of valine; 1.5 parts of L-tryptophan; 4.0 parts of L-phenylalanine; 3.0 parts of L-methionine; 6.5 parts of L-lysine; 5.0 parts of L-threonine; 7.0 parts of L-arginine; 0.7 parts of L-tyrosine; 1.0 part of L-cysteine; 5.5 parts of L-alanine; 7.8 parts of L-glutamic acid; 3.5 parts of L-aspartic acid; 3.5 parts of L-histidine; 2.0 parts of L-serine; 3.0 parts of glycine and 2.0 parts of L-proline.

15. A composition according to claim 7 in which the amino acids comprise per unit packaged form 1.6 grams of L-isoleucine; 3.3 grams of L-leucine; 1.6 grams of valine; 0.2 grams of L-tryptophan; 0.6 grams of L-phenylalanine; 0.4 grams of L-methionine; 1.0 grams of L-lysine; 0.8 grams of L-threonine; 1.0 grams of L-arginine; 0.1 grams of L-tyrosine; 0.2 grams of L-cysteine; 0.8 grams of L-alanine; 1.2 grams of L-glutamic acid; 0.5 grams of L-aspartic acid; 0.5 grams of L-histidine; 0.3 grams of L-serine; 0.4 grams of glycine and 0.3 grams of L-proline.

* * * * *